United States Patent
Meyn, III et al.

(10) Patent No.: US 9,464,272 B2
(45) Date of Patent: Oct. 11, 2016

(54) CELL-DERIVED COMPOSITION

(71) Applicant: Stemnion, Inc., Pittsburgh, PA (US)

(72) Inventors: Malcolm A Meyn, III, Pittsburgh, PA (US); Christopher A Fried, Pittsburgh, PA (US); Donna M Olejniczak, Pittsburgh, PA (US); Randall G Rupp, Swanton, VT (US)

(73) Assignee: STEMNION, INC., Pittsburgh, PA (US)

( * ) Notice: Subject to any disclaimer, the term of this patent is extended or adjusted under 35 U.S.C. 154(b) by 45 days.

(21) Appl. No.: 14/567,457

(22) Filed: Dec. 11, 2014

(65) Prior Publication Data

US 2015/0166951 A1    Jun. 18, 2015

Related U.S. Application Data

(60) Provisional application No. 61/915,054, filed on Dec. 12, 2013.

(51) Int. Cl.
  *C12N 5/073* (2010.01)
  *A61K 35/50* (2015.01)
  *A61K 38/19* (2006.01)

(52) U.S. Cl.
  CPC ............ *C12N 5/0605* (2013.01); *A61K 35/50* (2013.01); *A61K 38/19* (2013.01); *C12N 2501/11* (2013.01); *C12N 2501/998* (2013.01); *C12N 2502/03* (2013.01)

(58) Field of Classification Search
  None
  See application file for complete search history.

(56) References Cited

U.S. PATENT DOCUMENTS

| | | | |
|---|---|---|---|
| 2012/0046601 A1* | 2/2012 | Sing | A61K 35/50 604/22 |
| 2012/0171180 A1* | 7/2012 | Abramson | A61K 35/16 424/93.72 |

OTHER PUBLICATIONS

Backesjo, C.-M. et al. 2006. Activation of Sirt1 decreases adipocyte formation during osteoblast differentiation of mesenchymal stem cells. Journal of Bone and Mineral Research 21(7): 993-1002. specif. pp. 993, 994.*

ThermoFisher Scientific.Basal medium Eagle (BME). Datasheet [online]. Copyright 2016 Thermo Fisher Scientific, Inc. [retrieved on Mar. 19, 2016]. Retrieved from the Internet: <URL: https://www.thermofisher.com/order/catalog/product/21010046>. p. 1.*

* cited by examiner

*Primary Examiner* — Renee Claytor
*Assistant Examiner* — Sharon M Papciak
(74) *Attorney, Agent, or Firm* — Linda O. Palladino; Gail M. Kempler

(57) ABSTRACT

The invention is directed to a cell-derived composition having bone growth, regeneration, and repair promoting properties. In particular, the invention is directed to a cell-derived composition having bone growth, regeneration, and repair promoting properties termed Amnion-derived Cellular Cytokine Solution-B (ACCS-B). The invention is further directed to the use of this composition to promote bone growth and/or regeneration and/or repair.

5 Claims, No Drawings

US 9,464,272 B2

CELL-DERIVED COMPOSITION

STATEMENT REGARDING FEDERALLY SPONSORED RESEARCH OR DEVELOPMENT

This invention was made in part with United States government support awarded by the following agency: US ARMY MEDICAL RESEARCH ACQUISITION ACT, contract no. W81XWH1110591. The United States may have certain rights to this invention.

FIELD OF THE INVENTION

The field of the invention is directed to a novel cell-derived composition having bone growth, regeneration, and repair promoting properties. In particular, the field of the invention is directed to a novel cell-derived composition having bone growth, regeneration, and repair promoting properties termed Amnion-derived Cellular Cytokine Solution-B (ACCS-B). The field of the invention is further directed to the use of this novel composition to promote bone growth and/or regeneration and/or repair.

BRIEF SUMMARY OF THE INVENTION

It is an object of the instant invention to provide a novel cell-derived composition having bone growth and/or regeneration and/or repair promoting properties. This novel cell-derived composition is created by culturing AMP cells under specific conditions such that genes important for bone growth and/or regeneration and/or repair promoting properties are up-regulated as compared to AMP cells cultured under standard conditions.

Accordingly, a first aspect of the invention is a composition comprising Amnion-derived Cellular Cytokine Solution-B (ACCS-B).

In a specific embodiment, the ACCS-B is a pharmaceutical composition.

In another specific embodiment, the ACCS-B pharmaceutical composition is contained in an article of manufacture, wherein the article of manufacture comprises the pharmaceutical composition, packaging material, and instructions for use of the pharmaceutical composition to promote bone growth, regeneration and/or repair.

In another specific embodiment, the ACCS-B is formulated for sustained-release (SR-ACCS-B).

A second aspect of the invention is a method for treating a bone injury comprising administering to a subject in need thereof a therapeutically effective dose of a composition selected from the group consisting of ACCS-B and SR-ACCS-B. In one embodiment the bone injury is a fracture. In another embodiment the bone injury is a surgical injury.

A third aspect of the invention is a method for making ACCS-B comprising the step of culturing Amnion-derived Multipotent Progenitor (AMP) cells in Basal Medium Eagle (BME) culture medium supplemented with human serum albumin and human EGF. In a specific embodiment, the human serum albumin is at 0.5% and the human EGF is at 10 ng/mL.

A fourth aspect of the invention is an ACCS-B composition made by aspect three of the invention.

Other features and advantages of the invention will be apparent from the accompanying description, examples and the claims. The contents of all references, pending patent applications and issued patents, cited throughout this application are hereby expressly incorporated by reference. In case of conflict, the present specification, including definitions, will control.

DEFINITIONS

As defined herein "isolated" refers to material removed from its original environment and is thus altered "by the hand of man" from its natural state.

As used herein, the term "protein marker" means any protein molecule characteristic of the plasma membrane of a cell or in some cases of a specific cell type.

As used herein, "enriched" means to selectively concentrate or to increase the amount of one or more materials by elimination of the unwanted materials or selection and separation of desirable materials from a mixture (i.e. separate cells with specific cell markers from a heterogeneous cell population in which not all cells in the population express the marker).

As used herein, the term "substantially purified" means a population of cells substantially homogeneous for a particular marker or combination of markers. By substantially homogeneous is meant at least 90%, and preferably 95% homogeneous for a particular marker or combination of markers.

The term "placenta" as used herein means both preterm and term placenta.

As used herein, the term "totipotent cells" shall have the following meaning In mammals, totipotent cells have the potential to become any cell type in the adult body; any cell type(s) of the extraembryonic membranes (e.g., placenta). Totipotent cells are the fertilized egg and approximately the first 4 cells produced by its cleavage.

As used herein, the term "pluripotent stem cells" shall have the following meaning Pluripotent stem cells are true stem cells with the potential to make any differentiated cell in the body, but cannot contribute to making the components of the extraembryonic membranes which are derived from the trophoblast. The amnion develops from the epiblast, not the trophoblast. Four types of pluripotent stem cells have been confirmed to date: Embryonic Stem (ES) Cells (may also be totipotent in primates), Embryonic Germ (EG) Cells, Embryonic Carcinoma (EC) Cells, and late Epiblast Stem Cells (EpiSCs). Recently, artificially produced pluripotent stem cells, called induced pluripotent cells (iPCs) have been created in the laboratory.

As used herein, the term "multipotent stem cells" are true stem cells but can only differentiate into a limited number of types. For example, the bone marrow contains multipotent stem cells that give rise to all the cells of the blood but may not be able to differentiate into other cells types.

As used herein, the term "extraembryonic tissue" means tissue located outside the embryonic body which is involved with the embryo's protection, nutrition, waste removal, etc. Extraembryonic tissue is discarded at birth. Extraembryonic tissue includes but is not limited to the amnion, chorion (trophoblast and extraembryonic mesoderm including umbilical cord and vessels), yolk sac, allantois and amniotic fluid (including all components contained therein). Extraembryonic tissue and cells derived therefrom have the same genotype as the developing embryo.

As used herein, the term "extraembryonic cytokine secreting cells" or "ECS cells" means a population of cells derived from the extraembryonic tissue which have the characteristics of secreting a unique combination of physiologically relevant cytokines in a physiologically relevant temporal manner into the extracellular space or into surrounding culture media and which have not been cultured in the presence of any animal-derived products, making them and cell products derived from them suitable for human clinical use. In a preferred embodiment, the ECS cells secrete the cytokines VEGF, Angiogenin, PDGF and TGFβ2 and the MMP inhibitors TIMP-1 and/or TIMP-2. The physiological range of the cytokine or cytokines in the unique combination is as follows: ~5-16 ng/mL for VEGF, ~3.5-4.5 ng/mL for Angiogenin, ~100-165 pg/mL for PDGF, ~2.5-2.7 ng/mL for TGFβ2, ~0.68 µg/mL for TIMP-1 and ~1.04 µg/mL for TIMP-2. The ECS cells may optionally express Thymosin β4.

As used herein, the term "Amnion-derived Multipotent Progenitor Cell" or "AMP cell" means a specific population of ECS cells that are epithelial cells derived from the amnion. In addition to the characteristics described above for ECS cells, AMP cells have the following characteristics. They have not been cultured in the presence of any animal-derived products, making them and cell products derived from them suitable for human clinical use. They grow without feeder layers, do not express the protein telomerase and are non-tumorigenic. AMP cells do not express the hematopoietic stem cell marker CD34 protein. The absence of CD34 positive cells in this population indicates the isolates are not contaminated with hematopoietic stem cells such as umbilical cord blood or embryonic fibroblasts. Virtually 100% of the cells react with antibodies to low molecular weight cytokeratins, confirming their epithelial nature. Freshly isolated amnion-epithelial cells will not react with antibodies to the stem/progenitor cell markers c-kit (CD117) and Thy-1 (CD90). Several procedures used to obtain cells from full term or pre-term placenta are known in the art (see, for example, US 2004/0110287; Anker et al., 2005, Stem Cells 22:1338-1345; Ramkumar et al., 1995, Am. J. Ob. Gyn. 172:493-500). However, the methods used herein provide improved, novel compositions and populations of cells.

By the term "animal-free" when referring to certain compositions, growth conditions, culture media, etc. described herein, is meant that no non-human animal-derived materials, such as non-human animal-derived serum, other than clinical grade human materials, such as recombinantly produced human proteins, are used in the preparation, growth, culturing, expansion, storage or formulation of the certain composition or process.

By the term "serum-free" when referring to certain compositions, growth conditions, culture media, etc. described herein, is meant that no non-human animal-derived serum is used in the preparation, growth, culturing, expansion, storage or formulation of the certain composition or process.

By the term "expanded", in reference to cell compositions, means that the cell population constitutes a significantly higher concentration of cells than is obtained using previous methods. For example, the level of cells per gram of amniotic tissue in expanded compositions of AMP cells is at least 50 and up to 150 fold higher than the number of cells in the primary culture after 5 passages, as compared to about a 20 fold increase in such cells using previous methods. In another example, the level of cells per gram of amniotic tissue in expanded compositions of AMP cells is at least 30 and up to 100 fold higher than the number of cells in the primary culture after 3 passages. Accordingly, an "expanded" population has at least a 2 fold, and up to a 10 fold, improvement in cell numbers per gram of amniotic tissue over previous methods. The term "expanded" is meant to cover only those situations in which a person has intervened to elevate the number of the cells.

As used herein, "conditioned medium" is a medium in which a specific cell or population of cells has been cultured, and then removed. When cells are cultured in a medium, they may secrete cellular factors that can provide support to or affect the behavior of other cells. Such factors include, but are not limited to hormones, cytokines, extracellular matrix (ECM), proteins, vesicles, antibodies, chemokines, receptors, inhibitors and granules. The medium containing the cellular factors is the conditioned medium. Examples of methods of preparing conditioned media are described in U.S. Pat. No. 6,372,494 which is incorporated by reference in its entirety herein. As used herein, conditioned medium also refers to components, such as proteins, that are recovered and/or purified from conditioned medium or from ECS cells, including AMP cells.

As used herein, the term "Amnion-derived Cellular Cytokine Solution" or "ACCS" means conditioned medium that has been derived from AMP cells or expanded AMP cells.

As used herein, "ACCS-B" means a novel composition that is created by culturing AMP cells in Basal Medium Eagle (BME) culture medium supplemented with 0.5% human serum albumin and 10 ng/mL recombinant human EGF.

As used herein, the term "suspension" means a liquid containing dispersed components, i.e. cytokines. The dispersed components may be fully solubilized, partially solubilized, suspended or otherwise dispersed in the liquid. Suitable liquids include, but are not limited to, water, osmotic solutions such as salt and/or sugar solutions, cell culture media, and other aqueous or non-aqueous solutions.

The term "lysate" as used herein refers to the composition obtained when cells, for example, AMP cells, are lysed and optionally the cellular debris (e.g., cellular membranes) is removed. This may be achieved by mechanical means, by freezing and thawing, by sonication, by use of detergents, such as EDTA, or by enzymatic digestion using, for example, hyaluronidase, dispase, proteases, and nucleases. In certain instances, it may be desirable to retain the cell membranes, as well.

The term "physiologic" or "physiological level" as used herein means the level that a substance in a living system is found and that is relevant to the proper functioning of a biochemical and/or biological process.

As used herein, the term "substrate" means a defined coating on a surface that cells attach to, grown on, and/or migrate on. As used herein, the term "matrix" means a substance that cells grow in or on that may or may not be defined in its components. The matrix includes both biological and non-biological substances. As used herein, the term "scaffold" means a three-dimensional (3D) structure (substrate and/or matrix) that cells grow in or on. It may be composed of biological components, synthetic components or a combination of both. Further, it may be naturally constructed by cells or artificially constructed. In addition, the scaffold may contain components that have biological activity under appropriate conditions.

The term "cell product" or "cell products" as used herein refers to any and all substances made by and secreted from a cell, including but not limited to, protein factors (i.e. growth factors, differentiation factors, engraftment factors, cytokines, morphogens, proteases (i.e. to promote endogenous cell delamination, protease inhibitors), extracellular matrix components (i.e. fibronectin, etc.), and the like.

The term "therapeutically effective amount" means that amount of a therapeutic agent necessary to achieve a desired physiological effect (i.e. to promote bone growth, regeneration, and/or repair).

As used herein, the term "pharmaceutically acceptable" means that the components, in addition to the therapeutic agent, comprising the formulation, are suitable for administration to the patient being treated in accordance with the present invention.

As used herein, the term "therapeutic component" means a component of the composition which exerts a therapeutic benefit when the composition is administered to a subject.

As used herein, the term "therapeutic protein" includes a wide range of biologically active proteins including, but not limited to, growth factors, enzymes, hormones, cytokines, inhibitors of cytokines, blood clotting factors, peptide growth and differentiation factors.

As used herein, the term "tissue" refers to an aggregation of similarly specialized cells united in the performance of a particular function.

As used herein, the terms "a" or "an" means one or more; at least one.

As used herein, the term "adjunctive" means jointly, together with, in addition to, in conjunction with, and the like.

As used herein, the term "co-administer" can include simultaneous or sequential administration of two or more agents.

As used herein, the term "agent" means an active agent or an inactive agent. By the term "active agent" is meant an agent that is capable of having a physiological effect when administered to a subject. Non-limiting examples of active agents include growth factors, cytokines, antibiotics, cells, conditioned media from cells, etc. By the term "inactive agent" is meant an agent that does not have a physiological effect when administered. Such agents may alternatively be called "pharmaceutically acceptable excipients". Non-limiting examples include time release capsules and the like.

The terms "parenteral administration" and "administered parenterally" are art-recognized and refer to modes of administration other than enteral and topical administration, usually by injection, and includes, without limitation, intravenous, intramuscular, intraosseous, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal injection or infusion.

As used herein, the term "enteral" administration means any route of drug administration that involves absorption of the drug through the gastrointestinal tract. Enteral administration may be divided into three different categories, oral, gastric, and rectal. Gastric introduction involves the use of a tube through the nasal passage or a tube in the abdomen leading directly to the stomach.

As used herein, the term "topical" administration means a medication that is applied to body surfaces such as the skin or mucous membranes to treat ailments via a large range of classes including but not limited to liquids, sprays, creams, foams, gels, lotions, salves and ointments. This can also include injection into the skin layers, i.e., subcutaneous.

The terms "sustained-release", "extended-release", "time-release", "controlled-release", or "continuous-release" as used herein means an agent, typically a therapeutic agent or drug, that is formulated to dissolve slowly and be released over time.

"Treatment," "treat," or "treating," as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; (c) relieving and or ameliorating the disease or condition, i.e., causing regression of the disease or condition; or (d) curing the disease or condition, i.e., stopping its development or progression. The population of subjects treated by the methods of the invention includes subjects suffering from the undesirable condition or disease, as well as subjects at risk for development of the condition or disease.

As used herein, a "wound" is any disruption, from whatever cause, of normal anatomy (internal and/or external anatomy) including but not limited to traumatic injuries such as mechanical (i.e. contusion, penetrating), thermal, chemical, electrical, radiation, concussive and incisional injuries; elective injuries such as operative surgery and resultant incisional hernias, fistulas, etc.; acute wounds, chronic wounds, infected wounds, and sterile wounds, as well as wounds associated with disease states (i.e. ulcers caused by diabetic neuropathy or ulcers of the gastrointestinal or genitourinary tract). A wound is dynamic and the process of healing is a continuum requiring a series of integrated and interrelated cellular processes that begin at the time of wounding and proceed beyond initial wound closure through arrival at a stable scar. These cellular processes are mediated or modulated by humoral substances including but not limited to cytokines, lymphokines, growth factors, and hormones. In accordance with the subject invention, "wound healing" refers to improving, by some form of intervention, the natural cellular processes and humoral substances of tissue repair such that healing is faster, and/or the resulting healed area has less scaring and/or the wounded area possesses tissue strength that is closer to that of uninjured tissue and/or the wounded tissue attains some degree of functional recovery.

As used herein the term "standard animal model" refers to any art-accepted animal model in which the compositions of the invention exhibit efficacy.

DETAILED DESCRIPTION

In accordance with the present invention there may be employed conventional molecular biology, microbiology, and recombinant DNA techniques within the skill of the art. Such techniques are explained fully in the literature. See, e.g., Sambrook et al, 2001, "Molecular Cloning: A Laboratory Manual"; Ausubel, ed., 1994, "Current Protocols in Molecular Biology" Volumes I-III; Celis, ed., 1994, "Cell Biology: A Laboratory Handbook" Volumes I-III; Coligan, ed., 1994, "Current Protocols in Immunology" Volumes I-III; Gait ed., 1984, "Oligonucleotide Synthesis"; Hames & Higgins eds., 1985, "Nucleic Acid Hybridization"; Hames & Higgins, eds., 1984, "Transcription And Translation"; Freshney, ed., 1986, "Animal Cell Culture"; IRL Press, 1986, "Immobilized Cells And Enzymes"; Perbal, 1984, "A Practical Guide To Molecular Cloning."

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Compositions and Methods of Making Compositions

Detailed information and methods on the preparation of AMP cell compositions, generation of ACCS, detection of cytokines in ACCS using ELISA and/or antibody array, and generation of sustained-release compositions can be found in U.S. Pat. Nos. 8,058,066 and 8,088,732, both of which are incorporated herein by reference in their entirety.

The invention provides for an article of manufacture comprising packaging material and a pharmaceutical composition of the invention contained within the packaging material, wherein the pharmaceutical composition comprises ACCS-B. The packaging material comprises a label or package insert which indicates that the ACCS-B contained therein can be used for therapeutic applications such as, for example, promoting bone growth, regeneration, and/or repair.

Formulation, Dosage and Administration

The compositions of the invention can be prepared in a variety of ways depending on the intended use of the compositions. For example, a composition useful in practicing the invention may be a liquid comprising an agent of the invention, i.e., ACCS-B, in solution, in suspension, or both (solution/suspension). The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment, salve, cream, or the like.

An aqueous suspension or solution/suspension of the invention may contain one or more polymers as suspending agents. Useful polymers include water-soluble polymers such as cellulosic polymers and water-insoluble polymers such as cross-linked carboxyl-containing polymers. An aqueous suspension or solution/suspension of the present invention may be viscous or mucoadhesive or both viscous and mucoadhesive.

Compositions comprising ACCS-B may be administered to a subject to provide various cellular or tissue functions, for example, to promote bone growth, regeneration, and/or repair. As used herein "subject" may mean either a human or non-human animal.

Such compositions may be formulated in any conventional manner using one or more physiologically acceptable carriers optionally comprising excipients and auxiliaries. Proper formulation is dependent upon the route of administration chosen. The compositions may be packaged with written instructions for their use to promote bone growth, regeneration, and/or repair. The compositions may also be administered to the recipient in one or more physiologically acceptable carriers. Carriers for the ACCS-B may include but are not limited to solutions of phosphate buffered saline (PBS) or lactated Ringer's solution containing a mixture of salts in physiologic concentrations, basal culture medium and the like.

Preferably the liquid composition is aqueous. Alternatively, the composition can take the form of an ointment. In a particular embodiment, the composition is an in situ gellable aqueous composition. Such a composition can comprise a gelling agent in a concentration effective to promote gelling upon contact with the body. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums. The phrase "in situ gellable" includes not only liquids of low viscosity that can form gels, but also more viscous liquids such as semi-fluid and thixotropic gels that exhibit substantially increased viscosity or gel stiffness upon administration.

Aqueous compositions of the invention have physiologically compatible pH and osmolality. Typically, these compositions incorporate means to inhibit microbial growth, for example through preparation and packaging under sterile conditions and/or through inclusion of an antimicrobially effective amount of an acceptable preservative. Suitable preservatives non-restrictively include mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

The composition can comprise a depot formulation comprising an active agent for administration. The depot formulation comprises a composition of the invention (i.e., ACCS-B). The microparticles comprising the compositions can be embedded in a biocompatible pharmaceutically acceptable polymer or a lipid encapsulating agent. The depot formulations may be adapted to release all or substantially all of the active material over an extended period of time. The polymer or lipid matrix, if present, may be adapted to degrade sufficiently to be transported from the site of administration after release of all, or substantially all, of the active agent. The depot formulation can be liquid formulation, comprising a pharmaceutical acceptable polymer and a dissolved or dispersed active agent. Upon injection, the polymer forms a depot at the injections site, e.g. by gelifying or precipitating.

The composition can comprise a solid article that can be inserted or implanted in a suitable location in the disease or injury site, where the article releases the active agent. Solid articles suitable for insertion or implantation generally comprise polymers and can be bioerodible or non-bioerodible. Bioerodible polymers that can be used in preparation of implants carrying a composition in accordance with the present invention include without restriction aliphatic polyesters such as polymers and copolymers of poly(glycolide), poly(lactide), poly(.epsilon.-caprolactone), poly(hydroxybutyrate) and poly(hydroxyvalerate), polyamino acids, polyorthoesters, polyanhydrides, aliphatic polycarbonates and polyether lactose. Illustrative of suitable non-bioerodible polymers are silicone elastomers.

Support matrices into which the ACCS-B can be incorporated or embedded include matrices which are recipient-compatible and which degrade into products which are not harmful to the recipient.

Natural and/or synthetic biodegradable matrices are examples of such matrices. Natural biodegradable matrices include plasma clots, e.g., derived from a mammal, collagen, fibronectin, and laminin matrices. Suitable synthetic matrix material must be biocompatible to preclude immunological complications. It must also be resorbable. The matrix should be configurable into a variety of shapes and should have sufficient strength to prevent collapse upon implantation. Recent studies indicate that the biodegradable polyester polymers made of polyglycolic acid fulfill all of these criteria (Vacanti, et al. J. Ped. Surg. 23:3-9 (1988); Cima, et al. Biotechnol. Bioeng. 38:145 (1991); Vacanti, et al. Plast. Reconstr. Surg. 88:753-9 (1991)). Other synthetic biodegradable support matrices include synthetic polymers such as polyanhydrides, polyorthoesters, and polylactic acid. Further examples of synthetic polymers and methods of incorporating or embedding compositions into these matrices are also known in the art. See e.g., U.S. Pat. Nos. 4,298,002 and 5,308,701.

One of the advantages of a biodegradable polymeric matrix is that ACCS-B can be incorporated directly into the support matrix so that it is slowly released as the support matrix degrades in vivo. In addition to the ACCS-B, other factors, including nutrients, growth factors, inducers of differentiation or de-differentiation (i.e., causing differentiated cells to lose characteristics of differentiation and acquire characteristics such as proliferation and more general function), products of secretion, immunomodulators, inhibitors of inflammation, regression factors, biologically active compounds which enhance or allow ingrowth of the lymphatic network or nerve fibers, hyaluronic acid, and drugs, which are known to those skilled in the art and commercially available with instructions as to what constitutes an effective amount, from suppliers such as Collaborative Research, Sigma Chemical Co., growth factors such as epidermal growth factor (EGF) and heparin binding epidermal growth factor like growth factor (HB-EGF), could be incorporated into the matrix or be provided in conjunction with the matrix. Similarly, polymers containing peptides such as the attachment peptide RGD (Arg-Gly-Asp) can be synthesized for use in forming matrices (see e.g. U.S. Pat. Nos. 4,988,621, 4,792,525, 5,965,997, 4,879,237 and 4,789,734).

In another example, the ACCS-B may be incorporated in a gel matrix (such as Gelfoam from Upjohn Company). A variety of encapsulation technologies have been developed (e.g. Lacy et al., Science 254:1782-84 (1991); Sullivan et al., Science 252:718-712 (1991); WO 91/10470; WO 91/10425; U.S. Pat. No. 5,837,234; U.S. Pat. No. 5,011,472; U.S. Pat. No. 4,892,538). During open surgical procedures involving direct physical access to diseased or damaged tissue, all of the described forms of the ACCS-B delivery preparations are available options. These compositions can be repeatedly administered at intervals until a desired therapeutic effect is achieved, for example, to promote bone growth, regeneration, and/or repair.

The three-dimensional matrices to be used are structural matrices that provide a scaffold to guide the process of tissue healing and formation. Scaffolds can take forms ranging from fibers, gels, fabrics, sponge-like sheets, and complex 3-D structures with pores and channels fabricated using complex Solid Free Form Fabrication (SFFF) approaches. As used herein, the term "scaffold" means a three-dimensional (3D) structure (substrate and/or matrix). It may be composed of biological components, synthetic components or a combination of both. Further, it may be naturally constructed by cells or artificially constructed. In addition, the scaffold may contain components that have biological activity under appropriate conditions. The structure of the scaffold can include a mesh, a sponge or can be formed from a hydrogel.

The polymeric matrix may be made flexible or rigid, depending on the desired final form, structure and function. For repair of a defect, for example, a flexible fibrous mat is cut to approximate the entire defect then fitted to the surgically prepared defect as necessary during implantation. An advantage of using the fibrous matrices is the ease in reshaping and rearranging the structures at the time of implantation.

The invention also provides for the delivery of ACCS-B in conjunction with any of the above support matrices as well as amnion-derived membranes. Such membranes may be obtained as a by-product of the process described herein for the recovery of AMP cells, or by other methods, such as are described, for example, in U.S. Pat. No. 6,326,019 which describes a method for making, storing and using a surgical graft from human amniotic membrane, US 2003/0235580 which describes reconstituted and recombinant amniotic membranes for sustained delivery of therapeutic molecules, proteins or metabolites, to a site in a host, U.S. 2004/0181240, which describes an amniotic membrane covering for a tissue surface which may prevent adhesions, exclude bacteria or inhibit bacterial activity, or to promote healing or growth of tissue, and U.S. Pat. No. 4,361,552, which pertains to the preparation of cross-linked amnion membranes and their use in methods for treating burns and wounds. In accordance with the present invention, ACCS-B may be incorporated into such membranes.

One of skill in the art may readily determine the appropriate concentration, or dose, of the ACCS-B, for a particular purpose. The skilled artisan will recognize that a preferred dose is one which produces a therapeutic effect, such as promoting bone growth, regeneration, and/or repair, in a patient in need thereof. Of course, proper doses of the ACCS-B will require empirical determination at time of use based on several variables including but not limited to the severity and type of disease, injury, disorder or condition being treated; patient age, weight, sex, health; other medications and treatments being administered to the patient; and the like. One of skill in the art will also recognize that number of doses (dosing regimen) to be administered needs also to be empirically determined based on, for example, severity and type of disease, injury, disorder or condition being treated. In one embodiment, one dose is sufficient. Other embodiments contemplate, 2, 3, 4, or more doses.

The present invention provides a method of promoting bone growth, regeneration, and/or repair by administering to a subject ACCS-B in a therapeutically effective amount. By "therapeutically effective amount" is meant the dose of ACCS-B which is sufficient to elicit a therapeutic effect. Thus, the concentration of ACCS-B in an administered dose unit in accordance with the present invention is effective in, for example, to promote bone growth, regeneration, and/or repair.

In addition, one of skill in the art may readily determine the appropriate dose of the ACCS-B for a particular purpose. For example, a preferred dose for topical administration is in the range of about 0.1-to-1000 micrograms per square centimeter of applied area. Other preferred dose ranges are 1.0-to-50.0 micrograms/applied area. In a particular embodiment, it is expected that relatively small amounts of the ACCS-B will be therapeutically useful. One of skill in the art will also recognize that the number of doses to be administered needs also to be empirically determined based on, for example, severity and type of disease, disorder or injury being treated. For example, in a specific embodiment, one dose is sufficient to have a therapeutic effect. Other specific embodiments contemplate, 2, 3, 4, or more doses for therapeutic effect.

In further embodiments of the present invention, it may be desirable to co-administer other agents, including active agents and/or inactive agents, with the ACCS-B to promote bone growth, regeneration, and/or repair. Active agents include but are not limited to cytokines, chemokines, antibodies, inhibitors, antibiotics, anti-fungals, anti-virals, immunosuppressive agents, various cell types, and the like. Inactive agents include carriers, diluents, stabilizers, gelling agents, delivery vehicles, ECMs (natural and synthetic), scaffolds, matrices, nanoparticles and the like. When the ACCS-B is administered conjointly with other pharmaceutically active agents, even less of the ACCS-B may be needed to be therapeutically effective.

ACCS-B can be administered by injection into a target site of a subject via a delivery device, such as a tube, catheter, syringe, needle, atomizer, nebulizer, and the like, through which the ACCS-B can be introduced into the subject at a desired location.

Routes of administration include enteral, topical, intranasal, transmucosal, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, epidural, intracerebral and intrasternal administration. The appropriate route of administration will depend upon the disease, disorder, injury and site being treated.

The timing of administration of ACCS-B will depend upon the type and severity of the bone defect or injury being treated. In a particular embodiment, the ACCS-B is administered as soon as possible after a defect is diagnosed or an injury occurs. In other particular embodiments, the ACCS-B is administered more than one time following diagnosis or injury.

Sustained-Release Compositions

The ACCS-B may be formulated as a sustained-release composition. Skilled artisans are familiar with methodologies to create sustained-release compositions of therapeutic agents, including protein-based therapeutic agents such as ACCS-B.

The sustained-release compositions may be made by any of the methods described herein. For example, multivesicular liposome formulation technology is useful for the sustained-release of protein and peptide therapeutics. Qui, J., et al, (ACTA Pharmacol Sin, 2005, 26(11):1395-401) describe this methodology for the formulation of sustained-release interferon alpha-2b. Vyas, S. P., et al, (Drug Dev Ind Pharm, 2006, 32(6):699-707) describe encapsulating pegylated interferon alpha in multivesicular liposomes. ACCS-B is suitable for use in multivesicular liposome sustained-release formulations.

Nanoparticle technology is also useful for creating sustained-release compositions. For example, Packhaeuser, C. B., et al, (J Control Release, 2007, 123(2):131-40) describe biodegradable parenteral depot systems based on insulin loaded dialkylaminoalkyl-amine-poly(vinyl alcohol)-g-poly (lactide-co-glycolide) nanoparticules and conclude that nanoparticle-based depots are suitable candidates for the design of controlled-release devices for bioactive macromolecules (i.e. proteins). Dailey, L. A., et al, (Pharm Res 2003, 20(12):2011-20) describe surfactant-free, biodegradable nanoparticles for aerosol therapy which is based on the branched polymers DEAPA-PVAL-g-PLGA and conclude that DEAPA-PVAL-g-PLGA are versatile drug delivery systems. ACCS-B is suitable for use in nanoparticle-based sustained-release formulations.

Polymer-based sustained-release formulations are also very useful. Chan, Y. P., et al, (Expert Opin Drug Deliv, 2007, 4(4):441-51) provide a review of the Medusa system (Flamel Technologies), which is used for sustained-release of protein and peptide therapies. Thus far, the Medusa system has been applied to subcutaneous injection of IL-2 and IFN-alpha(2b), in animal models (rats, dogs, monkeys), and in clinical trials in renal cancer (IL-2) and hepatitis C (IFN-alpha(2b)) patients. Chavanpatil, M. D., et al, (Pharm Res, 2007, 24(4):803-10) describe surfactant-polymer nanoparticles as a novel platform for sustained and enhanced cellular delivery of water-soluble molecules. Takeuchi, H., et al, (Adv Drug Deliv Res, 2001, 47(1):39-54) describe mucoadhesive nanoparticulate systems for peptide drug delivery, including liposomes and polymeric nanoparticles. Wong, H. L., et al, (Pharm Res, 2006, 23(7):1574-85) describe a new polymer-lipid hybrid system which has been shown to increase cytotoxicity of doxorubicin against multidrug-resistant breast cancer cells. ACCS-B is suitable for use in the aforementioned sustained-release formulation methodologies.

In addition, other sustained-release methodologies familiar to skilled artisans, while not specifically described herein, are also suitable for use with ACCS-B.

Pharmaceutical Compositions—The present invention provides for a pharmaceutical composition of ACCS-B and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the composition is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin, and still others are familiar to skilled artisans.

Pharmaceutical compositions useful in the practice of certain embodiments of the invention (i.e. those embodiments utilizing topical administration) include a therapeutically effective amount of an active agent with a pharmaceutically acceptable carrier. Such pharmaceutical compositions may be liquid, gel, ointment, salve, slow release/sustained release formulations or other formulations suitable for administration to promote bone growth, regeneration, and/or repair. The pharmaceutical composition comprises a composition of the invention (i.e., ACCS-B) and, optionally, at least one pharmaceutically acceptable excipient.

The pharmaceutical composition of the invention can be formulated in neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Treatment Kits—The invention also provides for an article of manufacture or a kit comprising packaging material and a pharmaceutical composition of the invention contained within the packaging material, wherein the pharmaceutical composition comprises compositions ACCS-B. The packaging material comprises a label or package insert which indicates that the ACCS-B can be used to promote bone growth, regeneration, and/or repair.

Exemplary Therapeutic Uses of ACCS-B

Fractures—

The most common bone injury is fracture. A bone fracture can be the result of high force impact or stress, or injury as a result of certain medical conditions that weaken the bones, such as osteoporosis, bone cancer, or osteogenesis imperfecta, where the fracture is then properly termed a pathologic fracture. Treatment of bone fractures are broadly classified as surgical or conservative, the latter referring to any non-surgical procedure, such as pain management, immobilization or other non-surgical stabilization. A similar classification is "open" versus "closed" treatment. Open treatment refers to any treatment in which the fracture site is surgically opened, regardless of whether the fracture itself is an open (through the skin) or closed (not through the skin) fracture. Some fractures can lead to serious complications including a condition known as compartment syndrome which if not treated can lead to amputation of the affected limb. Other complications may include non-union, where the fractured bone fails to heal, or mal-union, where the fractured bone heals in a deformed manner. It is an object of the instant invention to administer ACCS-B to aid in the healing of fractured bones.

Surgery—

Bone is often injured as a result of a surgical procedure, for example, removal of a tumor from bone. A bone tumor is a neoplastic growth of tissue in bone. Abnormal growths found in the bone can be either benign or malignant. Treatment for some bone cancers may involve surgery, such as limb amputation, or limb sparing surgery (often in combination with chemotherapy and radiation therapy). Limb sparing surgery, or limb salvage surgery, means the limb is spared from amputation. Instead of amputation the affected bone is removed and is done in two ways (a) bone graft, in which a bone from elsewhere from the body is taken or (b) artificial bone is put in. In upper leg surgeries, limb salvage prostheses are available. It is an object of the instant invention to administer ACCS-B to aid in the healing of surgically injured bones.

Periodontal Disease—

The compositions of the invention are useful in preventing, reversing, ameliorating or treating dental diseases, disorders, or injuries, including but not limited to gingivitis and periodontitis.

Skilled artisans will recognize that any and all of the standard methods and modalities for promoting bone growth, regeneration, and/or repair currently in clinical practice and clinical development are suitable for practicing the methods of the invention. Routes of administration, formulation, co-administration with other agents (if appropriate) and the like are discussed in detail elsewhere herein.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of AMP Cell Compositions

Amnion epithelial cells were dissociated from starting amniotic membrane using the dissociation agent PXXIII. The average weight range of an amnion was 18-27 g. The number of cells recovered per g of amnion was about $10\text{-}15 \times 10^6$.

Method of obtaining selected AMP cells—Amnion epithelial cells were plated immediately upon isolation from the amnion. After ~2-3 days in culture non-adherent cells were removed and the adherent cells were kept. This attachment to a plastic tissue culture vessel is the selection method used to obtain the desired population of AMP cells for culture. Adherent and non-adherent AMP cells appear to have a similar cell surface marker expression profile but the adherent cells have greater viability and are the desired population of cells. Adherent AMP cells were cultured in basal medium supplemented with human serum albumin until they reached 120,000-150,000 cells/cm$^2$. At this point, the cultures were confluent. Suitable cell cultures will reach this number of cells between ~5-14 days. Attaining this criterion is an indicator of the proliferative potential of the AMP cells and cells that do not achieve this criterion are not selected for further analysis and use. Once the AMP cells reached 120,000-150,000 cells/cm$^2$, they were collected and cryopreserved. This collection time point is called p0.

Example 2

Preparation of ACCS-B

ACCS-B was prepared by culturing AMP cells in Basal Medium Eagle (BME) culture medium supplemented with 0.5% human serum albumin (HSA) and 10 ng/mL recombinant human EGF. Spent medium was replaced with fresh medium every 3 days. Conditioned medium (ACCS-B) was collected at 15 and 21 days of culture and evaluated by ELISA for the presence of secreted factors.

Example 3

Evaluation of ACCS-B for the Presence of Secreted Protein Factors

ACCS-B was evaluated using standard ELISA to identify secreted factors.

Results:

VEGF was detected at about 5567 pg/mL, Angiogenin was detected at about 302 pg/mL, PDGF-BB was detected at about 25 pg/mL, TIMP-1 was detected at about 314,433 pg/mL and TIMP-2 was detected at about 95,807 pg/mL. Angiogenin, PDGF-BB, TIMP-1 and TIMP-2 were all present at levels significantly different from those found in ACCS, which is about 3.5-4.5 ng/mL (3500-4500 pg/mL) for Angiogenin, about 100-165 pg/mL for PDGF, about 0.68 µg/mL (680,000 pg/mL) for TIMP-1, and about 1.04 µg/mL (1,040,000 pg/mL) for TIMP-2.

Example 4

Evaluation of Bone-Related Gene Expression in Cultured Cells

In addition, the AMP cells that had been cultured in Basal Medium Eagle (BME) culture medium supplemented with 0.5% HSA and 10 ng/mL recombinant human EGF were harvested at day 21 of culture, RNA was isolated and gene expression analysis was performed to look for expression of the following genes critical for bone growth, regeneration, and/or repair: RunX, osteopontin (OPN), osteoclastin (OCN), BMP2 and BMP4. AMP cells cultured under normal conditions were used as a comparator.

Results:

OPN, OCN and BMP2 gene expression was up-regulated in the BME-cultured cells as compared to AMP cells ($p=<0.05$). RunX2 and BMP4 were also up-regulated, but they were not statistically significant in this experiment.

Example 5

Evaluation of ACCS-B in an In Vitro Assay of Bone Growth, Regeneration and/or Repair Method:

ACCS and ACCS-B (bone ACCS) were compared in a modified scratch assay using an ibidi® µ-dish insert. Normal human osteoblast (NHOst) cells were seeded onto either side of the µ-dish insert and grown to 100% confluent. Once confluent, the µ-dish insert was removed leaving a uniform gap down the center. The experimental treatments (100% of ACCS, ACCS-B, growth media or STM 100) were added to the cells and photos of cell growth, or gap closure, were taken at regular intervals from 0 to 48 hours. The amount of closure from cell growth into the gap was measured and compared to time 0 photos to calculate percent gap closure.

Results:

At the 24 hour time point, the ACCS-B treatment was near 60% closed and ACCS was at 80% closure.

Example 6

Inflammatory Model—Use of ACCS to Prevent Onset of Periodontal Disease in an Animal Model Objective:

The aim of this study was to evaluate the preventive role of ACCS in *Porphyromonas gingivalis* (*P. gingivalis*)-induced experimental periodontitis in rabbits Methods:

Eight New-Zealand White rabbits were distributed into 3 groups: 1. Untreated (n=2), 2. Control (unconditioned ACCS culture media) (n=3), and 3. ACCS (n=3). At baseline, all rabbits received silk ligatures bilaterally tied around mandibular second premolars under general anesthesia. The assigned test materials, ACCS or control, in volumes of 10 µL were topically applied to the ligated sites with a blunt needled-Hamilton Syringe from the time of ligature; control animals received ligature, but no treatment. Topical *P. gingivalis*-containing slurry (1 mL) was subsequently applied to induce the periodontal inflammation. The application of test materials and *P. gingivalis* continued for 6 weeks on an every-other-day schedule. At 6 weeks, following euthanasia, the mandibles were surgically harvested. Morphometric, radiographic and histologic evaluations were performed.

Results:

Macroscopic evaluations including soft tissue assessments, crestal bone and infrabony measurements showed significant periodontal breakdown induced by *P. gingivalis* in control and no treatment groups at 6 weeks compared to historical ligature-alone groups ($p=0.05$, $p=0.03$, respectively). ACCS application significantly inhibited soft tissue inflammation and prevented both crestal bone loss and infrabony defect formation compared to untreated and control groups ($p=0.01$, $p=0.05$, respectively). Histologic assessments and histomorphometric measurements supported the clinical findings; ACCS treated animals demonstrated significantly less inflammation in soft tissue and less bone loss compared to the untreated and control groups ($p=0.05$).

Conclusions:

Topical ACCS application prevents periodontal inflammatory changes and bone loss induced by *P. gingivalis* as shown both at clinical and histopathological level. ACCS has potential as a therapeutic approach for the prevention of periodontal diseases Example 7

Inflammatory Model—Use of ACCS to Stop Progression of or Reverse Periodontal Disease in an Animal Model Objective:

The aim of this study was to evaluate the therapeutic actions of ACCS in the treatment of periodontitis induced by *P. gingivalis*.

Methods:

The study was conducted using a two-phase rabbit periodontitis protocol: 1—Disease induction (6 weeks) and 2—Treatment (6 weeks). Periodontal disease was induced in 16 New-Zealand White rabbits by every-other-day application of topical *P. gingivalis* to ligatured mandibular premolars. At the end of Phase 1, 4 randomly selected rabbits were sacrificed to serve as the baseline disease group. For Phase 2, the remaining 12 rabbits were distributed into 3 groups (n=4), 1—Untreated, 2—Control (unconditioned ACCS culture media) and 3—ACCS treatment. At the end of Phase 2, morphometric, radiographic and histologic evaluations were performed on harvested mandibles.

Results:

The baseline disease group exhibited experimental periodontitis evidenced by tissue inflammation and bone loss. At the end of Phase 2, the untreated group showed significant disease progression characterized by increased soft and hard tissue destruction ($p=0.05$). The tissue inflammation and bone loss was significantly reduced by topical ACCS compared to baseline disease and untreated groups ($p=0.05$; $p=0.002$, respectively). The control treatment also arrested disease progression compared to untreated group ($p=0.01$), but there was no improvement in periodontal health compared to baseline disease (p=0.4). Histopathological assessments revealed similar findings; ACCS stopped the progression of inflammatory process (p=0.003) and reversed bone destruction induced by *P. gingivalis* (p=0.008). The ACCS-treated group had minimal osteoclastic activity limited to crestal area compared to untreated and control groups, which showed a profound osteoclastogenic activity at the bone crest as well as at interproximal sites.

Conclusions:

Topical application of ACCS stopped the progression of periodontal inflammation and resulted in tissue regeneration in rabbit periodontitis indicating its potential therapeutic efficacy.

Example 8

Evaluation of ACCS-B in an in Vivo Model for Bone Growth, Regeneration and/or Repair ACCS-B is evaluated in a standard in vivo model for bone growth, regeneration and/or repair. An example of a suitable in vivo model is the one described in, for example, Kisiel M, et al., 2013, Evaluation of Injectable Constructs for Bone Repair with a Subperiosteal Cranial Model in the Rat. PLoS ONE 8(8): e71683. doi:10.1371/journal.pone.0071683.

Example 9

Generation of Sustained-Release ACCS-B Composition

Sustained-release compositions of ACCS-B are produced by combining ACCS-B compositions with any of the sustained-release formulation technologies described herein (see Detailed Description) or otherwise familiar to skilled artisans.

Throughout the specification various publications have been referred to. It is intended that each publication be incorporated by reference in its entirety into this specification.

What is claimed is:

1. A composition comprising Amnion-derived Cellular Cytokine Solution-B (ACCS-B), wherein the composition is made by a method comprising the step of culturing Amnion-derived Multipotent Progenitor (AMP) cells in Basal Medium Eagle (BME) culture medium supplemented with human serum albumin and recombinant human EGF.

2. The composition of claim 1 which is a pharmaceutical composition.

3. The composition of claim 1 which is formulated for sustained-release (SR).

4. A method for promoting bone growth comprising administering to a subject in need thereof a therapeutically effective dose of a composition selected from the group consisting of ACCS-B and SR-ACCS-B.

5. A method for making ACCS-B comprising the step of culturing Amnion-derived Multipotent Progenitor (AMP) cells in Basal Medium Eagle (BME) culture medium supplemented with human serum albumin and recombinant human EGF.

* * * * *

UNITED STATES PATENT AND TRADEMARK OFFICE
CERTIFICATE OF CORRECTION

| | | |
|---|---|---|
| PATENT NO. | : 9,464,272 B2 | Page 1 of 1 |
| APPLICATION NO. | : 14/567457 | |
| DATED | : October 11, 2016 | |
| INVENTOR(S) | : Malcolm A. Meyn, III et al. | |

It is certified that error appears in the above-identified patent and that said Letters Patent is hereby corrected as shown below:

In the Specification

In the Statement Regarding Federally Sponsored Research or Development in Column 1, Line 9, delete the words "may have" and insert the word --has--.

Signed and Sealed this
First Day of May, 2018

Andrei Iancu
*Director of the United States Patent and Trademark Office*